United States Patent [19]

Reiner

[11] 4,274,715
[45] Jun. 23, 1981

[54] METHOD AND APPARATUS FOR THE PROJECTION OF OPTICAL TEST OBJECTS

[75] Inventor: Josef Reiner, Cologne, Fed. Rep. of Germany

[73] Assignee: Herbert Schwind GmbH & Co. KG, Aschaffenburg, Fed. Rep. of Germany

[21] Appl. No.: 25,644

[22] Filed: Mar. 30, 1979

[30] Foreign Application Priority Data

Apr. 7, 1978 [DE] Fed. Rep. of Germany ....... 2815121

[51] Int. Cl.³ .......................... A61B 3/02; A61B 3/10
[52] U.S. Cl. .......................................... 351/30; 351/13
[58] Field of Search .................. 351/1, 6, 7, 13, 16, 351/30

[56] References Cited

U.S. PATENT DOCUMENTS

| | | |
|---|---|---|
| 2,212,597 | 8/1940 | Hadda et al. |
| 3,524,702 | 8/1970 | Bellows et al. ........................ 351/13 |
| 3,572,910 | 3/1971 | Koester ................................. 351/13 |
| 3,737,217 | 6/1973 | Haines et al. ..................... 351/30 X |

FOREIGN PATENT DOCUMENTS

| | | |
|---|---|---|
| 1016462 | 9/1957 | Fed. Rep. of Germany . |
| 1962698 | 2/1967 | Fed. Rep. of Germany . |
| 1955859 | 5/1971 | Fed. Rep. of Germany . |
| 2042109 | 5/1971 | Fed. Rep. of Germany . |
| 2543903 | 4/1977 | Fed. Rep. of Germany . |
| 690966 | 4/1953 | United Kingdom . |

Primary Examiner—John K. Corbin
Assistant Examiner—Rodney B. Bovernick
Attorney, Agent, or Firm—Sprung, Felfe, Horn, Lynch & Kramer

[57] ABSTRACT

Method and apparatus for projecting or imaging optotypes so that they can be perceived in space under conditions of unimpeded vision without requiring, e.g., projection screens.

5 Claims, 1 Drawing Figure

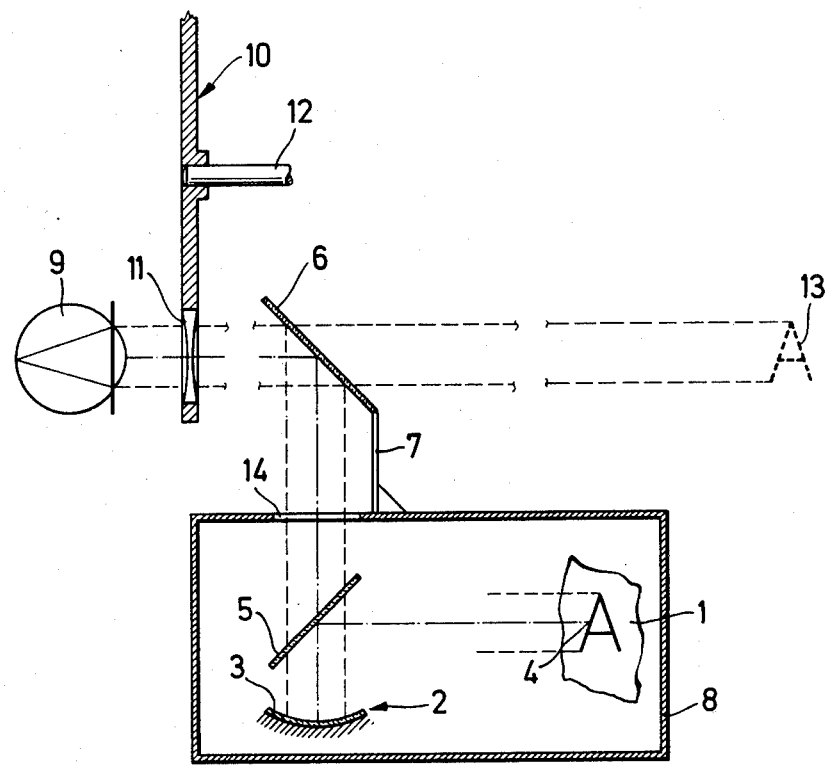

METHOD AND APPARATUS FOR THE PROJECTION OF OPTICAL TEST OBJECTS

This invention relates to a method for projecting optical test objects, as well as to an apparatus for executing this method.

Conventionally, optical test objects (optotypes) are rendered visible in a known manner on cardboard panels or backlighted glass sight-testing charts on the wall of a refraction area. Alternatively, they can be projected onto this wall by means of a diascope (slide projector). The test subject observes these optotypes during subjective refraction through corrrective lenses inserted into test spectacles or produced in a phoroptor. What is therefore required is a cardbroard chart on the wall or an illumination box for interchangeable indicia or a projection screen for projection with the aid of a diascope.

The invention provides a method and apparatus for projecting or imaging optotypes by means of which the optotypes can be perceived in space under conditions of unimpeded vision without requiring a special device such as cardboard or an illumination box or a projection screen on the wall of the refraction area.

The method of the invention comprises projecting the optotypes onto the retina of the eye to be examined by means of a collimator via a splitting mirror, with the eye looking into free space through said mirror.

The apparatus of the invention for projecting optotypes comprises a collimator in the object focal plane in which the optotypes are located, and by a first splitting mirror in the beam path of said collimator.

Further features and expedient developments of the invention will become evident from the description of an embodiment with reference to the drawing, in which:

The FIGURE shows a sectional view through the apparatus for projecting optotypes.

The apparatus includes a collimator 2 in a housing 8. The collimator consists of a concave mirror 3 with optotypes 1 positioned in the focal plane of said mirror which passes through the focal point 4 thereof. They optotypes can be arbitrarily illuminated optotypes, e.g., a slide illuminated from the rear by means of a suitable illumination means. The optotypes 1 are projected to the concave mirror via a semitransparent splitting mirror 5 which is inclined at an angle of 45° relative to the plane of the optotypes and the optical axis of the concave mirror 3. From the concave mirror, the optotypes 1 are then projected into infinity through the splitting mirror 5 and through an aperture 14 in the housing 8. Another splitting mirror 6, (hereinafter the first splitting mirror), attached to the housing with the aid of a mount 7, is provided in the parallel beam path issuing from said concave mirror and is inclined at an angle of 45° relative to the optical axis of the concave mirror. This deflects the parallel beam path with emerges vertically from the housing into a horizontally extending beam path.

For refraction, the apparatus is set up in the refraction area in such a way that the eye 9 of the test subject to be examined looks through the interposed corrective lens 11 on the one hand and, on the other hand, looks into the beam path issuing from the first splitting mirror 6. The corrective lens 11 can be located in test spectacles or, as in the illustrated embodiment, in a phoroptor which can be rotated about a shaft 12. After adjustment of the corrective lens 11 appropriate for the visual defect, the parallel beams issuing from the concave mirror 3 are projected upon the retina of the eye 9 such that the test subject has the impression that he is seeing the image 13 of the optotypes in the free space through the splitting mirror 6.

The concave mirror 3 and the two splitting mirrors 5 and 6 are selected to be so large that binocular vision of the optotypes is also possible. If desired, the apparatus can be modified in such a way that the beam path is separately split into two partial beam paths in order to examine each eye separately.

The collimator is designed as a concave mirror in the illustrated embodiment. However, it is also possible to use a collimator lens, the optotype then being located in the focal plane of the lens.

A commercial diascope (slide projector) with the objective lens removed can be employed to project the optotypes. This makes it possible to use a large number of different optotypes with rapid access by interchanging the slides.

It will be understood that the specification and examples are illustrative but not limitative of the present invention and that other embodiments within the spirit and scope of the invention will suggest themselves to those skilled in the art.

What is claimed is:

1. An apparatus for the projection of optotypes for use in the subjective determination of eye refraction, the apparatus comprising:
    a. a housing;
    b. a collimator disposed within the housing;
    c. means disposed within the housing the forming illuminated optotypes at the object focal plane of the collimator; and
    d. means coactive with the eye under examination and receptive of the image from the collimator for projecting same into free space in a line of sight defined by the eye and the projected image which is outside of said housing, the projecting means comprising means defining an output aperture in the housing through which the collimator image passes and a beam splitter mirror outisde of the housing and in said line of sight and receptive of the collimator image through the aperture.

2. The apparatus according to claim 1, wherein the beam splitter mirror is disposed at an angle of 45° with respect to the optical axis of the collimator.

3. The apparatus according to claim 1 or claim 2, wherein the collimator and beam splitter mirror are configured to permit binocular vision of the optotypes.

4. The apparatus according to claim 3, wherein the collimator comprises a concave reflector and further comprising a second beam splitter mirror for projecting the optotype image on the reflector.

5. A method for projecting optotypes for the subjective determination of eye refraction, the method comprising the steps of:
    a. providing a housing and a collimator therein;
    b. illuminating optotypes within the housing and at the object focal plane of the collimator; and
    c. projecting the image from the collimator into free space in a line of sight between the eye under examination and the projected image which is outside of said housing by providing an output aperture in the housing through which the collimator image passes and providing a beam splitter mirror outside of the housing in said line of sight and receptive of the collimator image through the aperture.

* * * * *